(12) United States Patent
Tellers et al.

(10) Patent No.: US 7,576,118 B2
(45) Date of Patent: Aug. 18, 2009

(54) ASYMMETRIC HYDROGENATION PROCESS

(75) Inventors: David M. Tellers, Cranford, NJ (US); Guy R. Humphrey, Hillsborough, NJ (US)

(73) Assignee: Merck & Co., Inc., Rahway, NJ (US)

( * ) Notice: Subject to any disclaimer, the term of this patent is extended or adjusted under 35 U.S.C. 154(b) by 531 days.

(21) Appl. No.: 11/097,565

(22) Filed: Apr. 1, 2005

(65) Prior Publication Data

US 2005/0222428 A1     Oct. 6, 2005

Related U.S. Application Data

(60) Provisional application No. 60/558,972, filed on Apr. 2, 2004.

(51) Int. Cl.
*A61K 31/403* (2006.01)
*C07D 209/82* (2006.01)

(52) U.S. Cl. ..................................... 514/411; 548/439

(58) Field of Classification Search ................ 548/439; 514/411

See application file for complete search history.

(56) References Cited

U.S. PATENT DOCUMENTS 4,962,230 A     10/1990     Takaya et al.

FOREIGN PATENT DOCUMENTS

WO     WO 03/062200 A2 *     7/2003
WO     WO 2005/013985 A1     2/2005

OTHER PUBLICATIONS

R. Noyori, et al., *J. Am. Chem. Soc.*, 108, pp. 7117-7119, (1986)—XP-002337343.

* cited by examiner

*Primary Examiner*—Joseph K. McKane
*Assistant Examiner*—Janet L Coppins
(74) *Attorney, Agent, or Firm*—Dianne Brown; Mark R. Daniel

(57) ABSTRACT

The present invention provides an asymmetric hydrogenation process for the preparation of chiral cycloalkanoindole DP receptor antagonists in high enantiomeric excess.

12 Claims, No Drawings

ASYMMETRIC HYDROGENATION PROCESS

CROSS REFERENCE TO RELATED APPLICATIONS

This application claims the benefit of U.S. Provisional Application No. 60/558,972, filed Apr. 2, 2004.

BACKGROUND OF THE INVENTION

Cycloalkanoindole derivatives having DP receptor antagonist activity are disclosed in PCT Application WO03/062200.

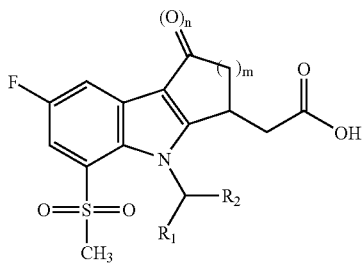

There exists a need for an efficient process for the preparation of such compounds enantioenriched in the desired stereoisomer.

SUMMARY OF THE INVENTION

The present invention provides a process for the preparation of chiral DP receptor antagonists and intermediates therefore by transition metal catalyzed enantioselective hydrogenation.

DETAILED DESCRIPTION OF THE INVENTION

The present invention provides an asymmetric hydrogenation process for the preparation of a compound of formula I or a salt thereof in at least 50% enantiomeric excess (ee)

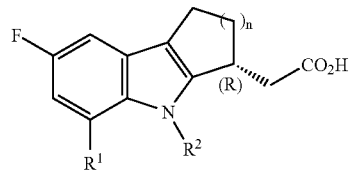

wherein n is 1 or 2, $R^1$ is H, Br or —$SO_2CH_3$, and $R^2$ is H, benzyl, 4-nitrobenzyl, 4-aminobenzyl, 4-trifluoromethylbenzyl or 4-chlorobenzyl, which comprises: treating a compound of formula II or a salt thereof

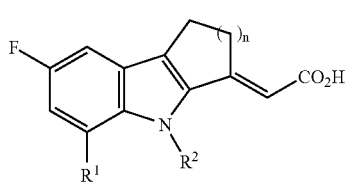

with a metal-chiral ligand and a hydrogen donor wherein when the hydrogen donor is $H_2$, the process is carried out at a pressure of from about 0 to about 500 pounds per square inch gauge (psig), and wherein said metal-chiral ligand is (a) a ruthenium-axially chiral phosphine ligand complex, or (2) a rhodium chiral ferrocenyl phosphine ligand complex, or (3) a rhodium-TMBTP complex.

Compounds of formula I wherein $R^1$ is —$SO_2CH_3$ and $R^2$ is 4-chlorobenzyl or 4-trifluoromethylbenzyl and pharmaceutically acceptable salts thereof are antagonists of the DP receptor and are useful in the treatment of allergic rhnitis, asthma, niacin-induced flushing, as well as other DP receptor mediated conditions, disorders and diseases. Compounds of formula I wherein $R^1$ is H, Br or $R^2$ is hydrogen, benzyl, 4-nitrobenzyl or 4-aminobenzyl are intermediates that may be subsequently transformed into the desired DP antagonists.

In one subset of the present process the metal-chiral ligand is ruthenium-axially chiral phosphine ligand complex. In one embodiment thereof the axially chiral ligand is selected from BINAP, tol-BINAP, xyl-BINAP, Synphos, Solvias BINAP, MeO-BIPHEP, hexaPHEMP, C(1-6)-tunaphos, P-Phos, xyl-P-Phos and TMBTP. In a second embodiment thereof the metal-chiral ligand is (p-cymene)Ru(axially chiral ligand)-$X_2$ where X is as defined below; preferably the ligand is selected from BINAP, tol-BINAP, xyl-BINAP, Synphos, Solvias BINAP, MeO-BIPHEP, hexaPHEMP, C(1-6)-tunaphos, P-Phos, xyl-P-Phos and TMBTP, and X is a halide such as chloride.

In a second subset of the present process the metal-chiral ligand is a rhodium-ferrocenylphosphine ligand complex. In one embodiment thereof the ferrocenylphosphine ligand is selected from f-BINAPHANE, Walphos, the josiphos of formula (k), and the taniaphos of formula (1).

In a third subset of the present process the metal-chiral ligand is a rhodium-TMBTP complex. In one embodiment the metal-chiral ligand is [(COD)Rh(TMBTP)]X, wherein X is as defined below; preferably X is a halide such as chloride.

In a fourth subset of the present process, the asymmetric hydrogenation is carried out in the presence of a base and optionally in the presence of a Group I or Group II salt.

In a fifth subset of the present process provides for the preparation of a compound of formula Ia or a salt thereof in at least 50% enantiomeric excess (ee)

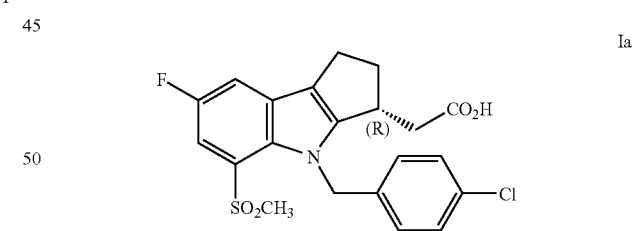

which comprises: treating a compound of formula IIa or a salt thereof

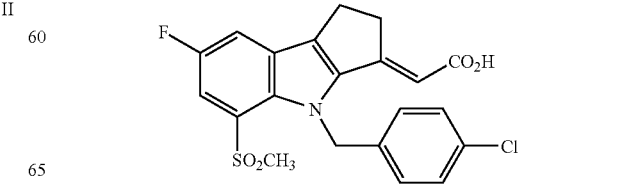

with a metal-chiral ligand and a hydrogen donor wherein when the hydrogen donor is H$_2$, the process is carried out at a pressure of from about 0 to about 500 pounds per square inch gauge (psig), and wherein said metal-chiral ligand is (a) a ruthenium-axially chiral phosphine ligand complex, or (2) a rhodium chiral ferrocenyl phosphine ligand complex, or (3) a rhodium-TMBTP complex.

In one embodiment thereof the asymmetric hydrogenation of compound IIa to form compound Ia is carried out using a ruthenium-axially chiral phosphine ligand wherein said ligand is selected from BINAP, tol-BINAP, xyl-BINAP, Synphos, Solvias BINAP, 5-Cl,6-MeO-BBPHEP, MeO-BIPHEP, hexaPHEMP, C(1-6)-tunaphos, P-Phos, xyl-P-Phos and TMBTP. The metal-chiral ligand is for example (p-cymene) Ru(axially chiral ligand)-X2 where X is as defined below; preferably the chiral ligand is BINAP, tol-BINAP, xyl-BINAP, Synphos, Solvias BINAP, MeO-BIPHEP, hexaPHEMP, C(1-6)-tunaphos, P-Phos, xyl-P-Phos and TMBTP, and X is a halide such as chloride.

In a second embodiment thereof the metal-chiral ligand is (1) rhodium-ferrocenyl-phosphine ligand wherein said ligand is selected from f-BINAPHANE, Walphos, the josiphos of formula (k), and the taniaphos of formula (1); or (2) a rhodium-TMBTP complex.

In a third embodiment thereof the asymmetric hydrogenation of compound IIa to form compound Ia is carried out with hydrogen at a pressure of from 0 to about 500 psig; for example from about 0 to about 250 psig, or from 0 to about 50 psig, or from 0 to about 20 psig, or from 0 to about 10 psig; the metal-chiral ligand is selected from (1) ruthenium complex with BINAP, tol-BINAP, xyl-BINAP, Synphos, Solvias BINAP, MeO-BIPHEP, hexaPHEMP, C(1-6)-tunaphos, P-Phos, xyl-P-Phos or TMBTP; (2) rhodium complex with f-BINAPHANE, Walphos, the josiphos of formula (k), the taniaphos of formula (1); or TMBTP. The asymmetric hydrogenation is preferably carried out in the presence of a base.

In the present process the "metal-chiral ligand" is an optically active ruthenium- or rhodium-phosphine complex that is either pre-formed from, or formed in situ by combining, a catalyst precursor and a chiral ligand. The metal-chiral ligand is generally used in an amount of from about 0.001 to about 100 mol %; preferably from about 0.2 to about 5 mol %, for example about 0.5 mol %.

Suitable catalyst precursors include, but are not limited to [Ru(L')X$_2$]$_2$, RuX$_3$, Ru(L')(allyl)$_2$, Rh(COD)$_2$X, Rh(NBD)$_2$X, [Rh(COD)X]$_2$, [Rh(NBD)X]$_2$, [Rh(COE)$_2$X]$_2$, [Rh(ethylene)$_2$X]$_2$ and [Rh(thiophene)$_2$X]$_2$, wherein COD is 1,5-cyclooctadiene, NBD is norbornadiene, and COE is cyclooctene; X is Cl, Br, I, triflate, acetate, methanesulfonate, benzenesulfonate, BF$_4$, or B(Ar)$_4$, and L' is arenes (for example benzene, toluene, cymene, xylenes, chlorobenzene, dichlorobenzene), nitriles (for example acetonitrile), ethers (for example tetrahydrofuran, methyl t-butyl ether, ethyl ether), amines (for example, triethylamine, diisopropyl ethylamine), alkenes (for example, ethylene, butene, cyclooctene, styrene, norbornene), or allyls (for example methylallyl). Examples of suitable preformed metal-chiral ligand include, but are not limited to, (chiral ligand) RuX$_2$, (chiral ligand) RuX$_2$(Y) wherein Y is dimethylformamide, triethylamine, dimethylsulfoxide or acetone, and X is as defined above. The ruthenium and rhodium catalyst precursors are well known in the art, and are either commercially available or may be prepared following known literature procedures.

"Axially chiral phosphine ligand" means an optically active diphosphine whose optical activity results from restricted rotation about single bond giving rise to isolable enantiomers. Examples of axially chiral phosphine ligands include, but are not limited to, those shown in Table 1, wherein Ar is for example phenyl, m- or p-toyl, xylyl and methoxyphenyl; Z is for example methyl, trifluoromethyl or methoxy; R$^a$ and R$^b$ are independently H, methyl, trifluoromethyl or methoxy, and R$^c$ is H or phenyl. Some specific examples are BINAP (formula (a) Ar=phenyl), tol-BINAP (formula (a) Ar=p-tolyl), xyl-BINAP (formula (a) Ar=3,5-xylyl), H8-BINAP (formula (b) Ar=phenyl), SYNPHOS™ (formula (c) Ar=phenyl), SEGPHOS (formula (d) Ar=phenyl), Solvias BINAP (formula (e) Ar=phenyl), Solvias xyl-BINAP (formula (e) Ar=3,5-xylyl), MeO-BIPHEP (formula (f) Ar=phenyl, Z=methyl, R$^a$=R$^b$=R$^c$=H), hexaPHEMP (formula (f) Ar=phenyl, Z=R$^a$=R$^b$=methyl, R$^c$=H), tunaphos (formula (g) Ar=phenyl and n is 1-6), TMBTP (formula (h) Ar=phenyl), P-Phos (formula (i) Ar=phenyl), tol-P-Phos (formula (i) Ar=tolyl), xyl-P-Phos (formula (i) Ar=3,5-xylyl).

TABLE 1

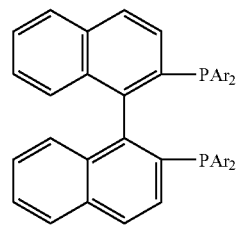

(a)

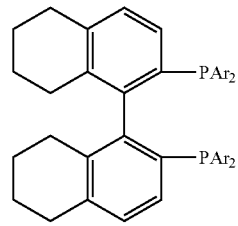

(b)

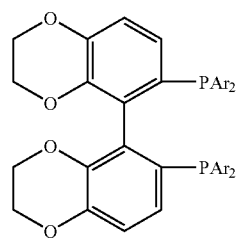

(c)

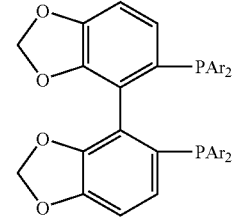

(d)

TABLE 1-continued
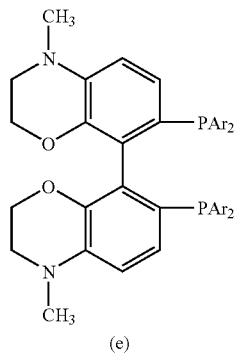
(e)
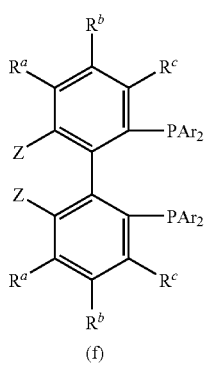
(f)
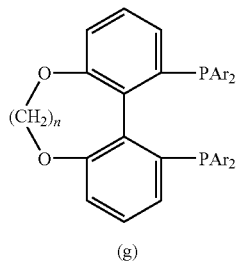
(g)
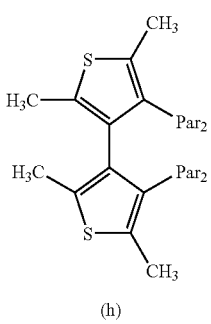
(h)
TABLE 1-continued
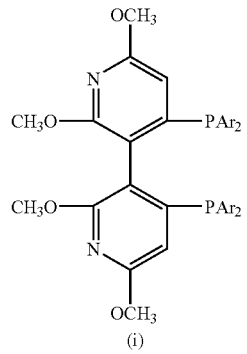
(i)
"Ferrocenyl phosphine ligands" include, but are not limited to, those shown in Table 2, namely, Walphos (formula (j) wherein $R^d$ and $R^e$ are each methyl or trifluoromethyl), the josiphos of formula (k), the taniaphos of formula (l), and f-BINAPHANE (m).
TABLE 2
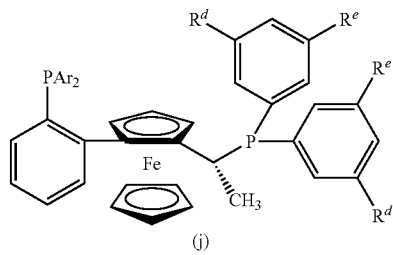
(j)
(k)
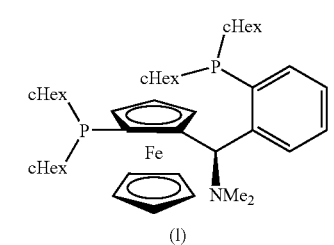
(l)
(m)

The metal-chiral ligands suitable for the present invention are either commercially available or may be prepared from a catalyst precursor and a chiral ligand by methods well known in the art, and described in the Reference Examples hereinbelow.

The hydrogen donor may be hydrogen gas, formic acid or a salt thereof such as sodium formate, or cyclohexadiene. Preferably hydrogen gas is used. Compounds of formula II may be prepared by following the procedure described in Reference Example 1

The asymmetric hydrogenation process may optionally include a base, which may be an inorganic or organic base. Salts of compounds of formulas I and II are formed with such bases. Inorganic bases are, for example, Group I or II hydroxides, alkoxides, aryloxides, alkyl anions, aryl anions, phosphonium, ammonium and sulfonium derived ylides. Organic bases include, for example, 1,1,3,3-tetramethylguanidine (TMG), 2,3,4,6,7,8,9,10-octahydropyrimidol[1,2-a]azepine (DBU), 1,5-diaza-bicyclo[4.3.0]non-5-ene (DBN), arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, phenethylamine, methylglucamine, morpholine, piperazine, piperidine, polyamine resins, procaine, purines, theobromine, triethylamine, trimethylamine, tripropylamine, tromethamine, α-methylbenzyl amine, 1,4-diazabicyclo[2.2.2]octane, (DABCO), butylamine, dibutylamine, dimethylphenylamine, diisopropylamine, diisopropylmethylamine, proton sponge, dimethylaminopyridine, tert-butylamine, tri-n-butylamine, triethanolamine, trimethylpyridine, imidazole, N-methylimidazole, tetramethylpiperdine. The asymmetric hydrogenation may additionally include a salt, which may be selected from Group I or Group II halides, triflates, sulfonates, acetates, and borates.

The asymmetric hydrogenation is carried out in an organic solvent with or without a co-solvent. Suitable organic solvents include alcohols such as methanol, ethanol, n-propanol, isopropanol, t-butanol; esters such as ethyl acetate and isopropyl acetae; amides such as dimethylformamide and dimethylacetamide; halogenated hydrocarbons such as dichloromethane, dichloroethane, and dichloro-benzene; ethers methyl t-butyl ether and tetrahydrofuran; ketones such as acetone and 2-butanone; arenes such as benzene, toluene, xylene; aliphatic hydrocarbons hexane and heptane; nitriles such as acetonitrile; and sulfoxides such as dimethylsulfoxide. The above solvents may be used alone or in a mixture of one or more solvents, or in combination with water. In one embodiment the asymmetric hydrogenation is carried out in a hydroxylic solvent such as methanol. The reaction temperature may be from about –20 to about 120° C.; preferably from about ambient temperature to about 70° C., and more preferably from about 40 to about 60° C. The reaction is generally complete within about 72 hours; usually the reaction time is from about 3 hours to about 24 hours.

The asymmetric hydrogenation when carried out with hydrogen is conducted at a pressure of from 0 to about 500 psig; in one embodiment the pressure is from about 0 to about 250 psig; in a second embodiment the pressure is from about 0 to about 150 psig; in a third embodiment the pressure is from about 0 to about 50 psig; in a fourth embodiment the pressure is from about 0 to about 20 psig; and in a fifth embodiment the pressure is from about 0 to about 10 psig. It has been found that enantioselectivity is inversely related to $H_2$ pressure; thus increasing hydrogen pressure generally results in decreased enantioselectivity, and $H_2$ pressure of above about 500 psig results in product mixture containing the desired enantiomer in less than 50% ee. Without being bound by theory the present inventors hypothesize that the compound of formula II (the E-isomer at the exocyclic double bond) undergoes transition metal catalyzed isomerization to the corresponding endo-isomer by going through the cyclopentene compound of formula III. The endo-isomer is the hydrogenation substrate that gives rise to the enantioenriched product of formula I. At low pressure isomerization of the E-isomer to the endo-isomer is faster than hydrogenation of the exocyclic double bond. Accordingly, in another embodiment of the present process the hydrogenation is carried out at a pressure of from 0 to about 20 psig; preferably from 0 to about 10 psig.

Another aspect of the present invention provides a process for the preparation of a compound of formula I or a salt thereof in at least 50% ee, comprising treating a compound of formula II or a salt thereof, a compound of formula III or a salt thereof, or a mixture thereof with hydrogen in the presence of a rhodium-chiral ligand complex or a ruthenium-chiral ligand complex and a base at a pressure of from about 0 to about 20 psi.

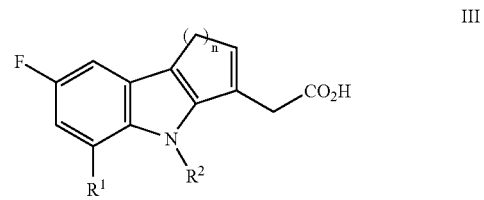

III

In this aspect on low pressure asymmetric hydrogenation, the pressure is preferably from 0 to about 10 psi, and all other reaction conditions are as discussed supra.

REFERENCE EXAMPLE 1

Preparation of Compound (13)

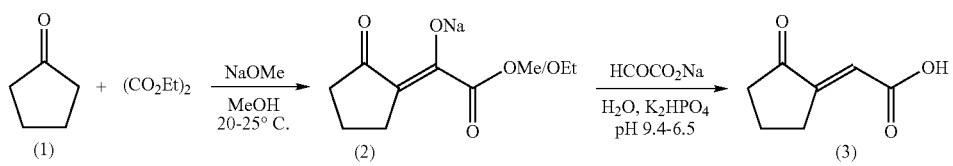

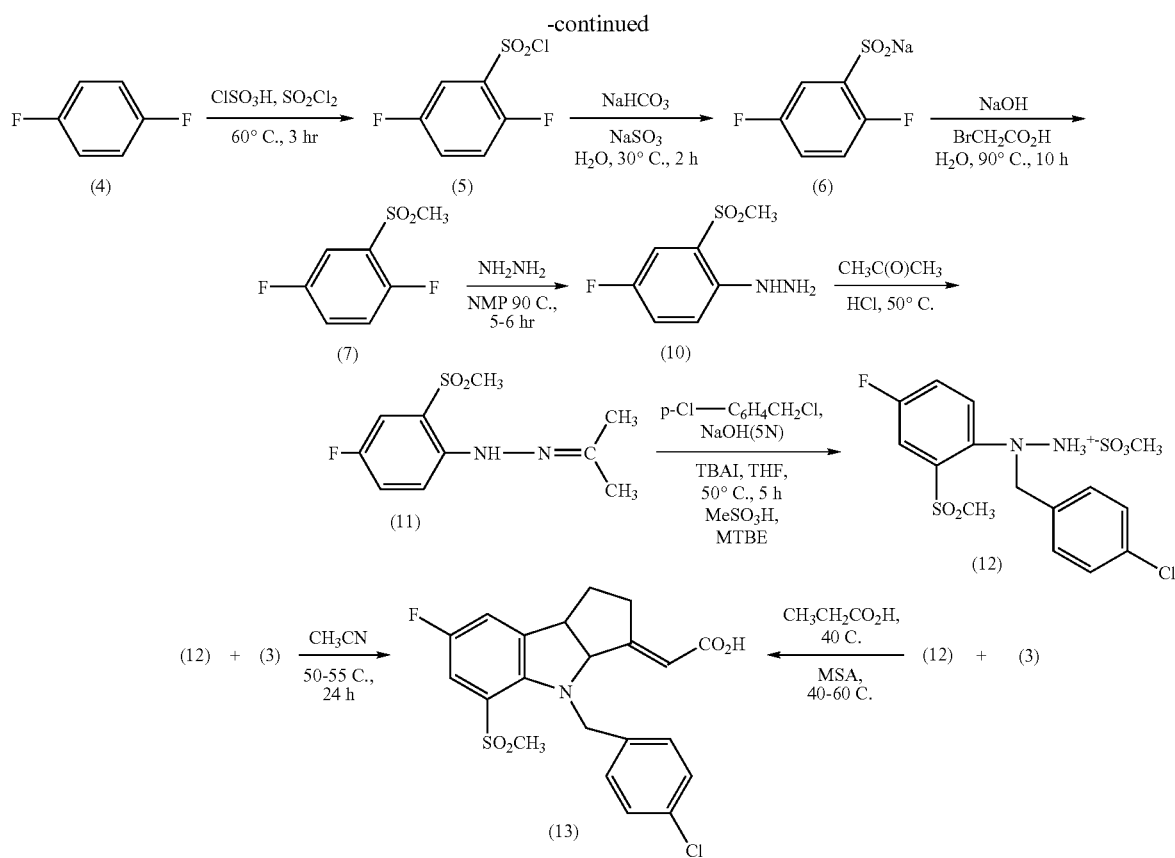

Step 1. Preparation of (2E)-(2-oxocyclopentylidene)acetic acid (compound 3)

A round-bottom flask was charged with toluene (12.5 ml/g cyclopentanone), cyclopentanone (1 eq.) and diethyloxalate (1 eq.). The colorless, homogeneous solution was stirred at 20° C. under nitrogen. Sodium methoxide (30 wt % in methanol, 1 eq.) was added via addition funnel over 1 h. The resultant slurry was warmed to 45° C. and aged for 1 h. The slurry was cooled to 15-20° C. and aged 1 h. The slurry was filtered and the cake washed with toluene (7.5 ml/g cyclopentanone). The cake was washed with toluene (7.5 ml/g cyclopentanone) and dried in a nitrogen stream for 1 h and in vacuo at 45° C. overnight to provide compound (2) as a pale yellow crystalline solid, and as approx 2:1 mixture of methyl to ethyl esters.

A round bottom flask was charged with glyoxylic acid (50 wt % solution in water, 1,28 eq.). Water (3.17 mL/mL of aqueous glyoxylic acid) was added and the solution cooled to 0-5° C. 5N sodium hydroxide (1.28 eq) was added slowly over about 1 h maintaining reaction temperature at less than 10° C. The pH was monitored during addition. Final pH was adjusted to 4.5 (+/−0.1). The resultant solution of sodium glyoxylate was cooled to −2° C. A separate vessel was charged with compound (2) (1 eq.) and deionized water (1 L/mole compound (2)) at room temperature. The solution was cooled to 10° C. Potassium phosphate dibasic (1.75 eq.) was added to the solution at 10° C. The resultant cloudy solution was cooled to −3° C., and the solution of sodium glyoxylate at −3° C. was added thereto over approximately 30 min. The batch was aged at −3 to 0° C. for 1 h post addition. The batch was warmed to 10° C. and methyl t-butyl ether (MTBE, 526 mL/mole compound (2)) added. Phosphoric acid (85%, 2.65 eq.) was added to adjust pH to 3.0 (+/−0.1). The phases were well mixed for 30 min and allowed to separate. The lower aqueous layer was extracted with MTBE (405 mmole compound (2)) and the MTBE layers combined. The MTBE layer was washed twice with 5% aqueous brine solution, and used 'as is'.

Step 2. Preparation of Compound (12)

To a round bottom flask under nitrogen is charged chlorosulfonic acid (3 eq.) followed by thionyl chloride (1.5 eq.). The solution was heated up to +55 to +60° C. and 1,4-difluorobenzene (1 eq.) was added dropwise over 2 hours. After completion of the addition, the reaction mixture was aged for 1 additional hour at +60° C. and allowed to cool to room temperature. The batch was added into a cooled (+5° C.) biphasic solution of methyl t-butyl ether (1 L/mole difluorobenzene) and water (1 L/mole difluorobenzene) over 1 hr. Layers are separated and the organic layer was washed with water (2×1 L/mole difluorobenzene).

In a separate vessel, a solution of sodium sulfite (1 eq.) and sodium bicarbonate (2 eq.) in water (1 L/mole difluorobenzene) was prepared. To this solution was added the MTBE layer containing compound (5) under stirring at ca. +25° C. over 1 hour. The biphasic solution was stirred for one additional hour at r.t and layers were separated. The aqueous solution containing compound (6) was used as is for the next step.

To the aqueous solution of compound (6) was added sodium hydroxide (50%, 1.2 eq.), and bromoacetic acid (1.2 eq.). The reaction mixture (pH-8.20) was heated up to +90° C., aged for 10 hours and allowed to cool to room temperature to crystallize the product, which was filtered, washed with water (0.5 L/mole difluorobenzene) and dried at +30-40° C. (m.p. ~60° C.) under vacuum to give compound (7).

To a round bottom Teflon flask was charged with N-methylpyrrolidinone (NMP, 800 mL/mole compound (7)), compound (7) (1 eq), and hydrazine (35% aqueous solution, 2.5 eq.). The solution was heated up to 90° C. and aged for 6 hours under nitrogen. The reaction mixture was then cooled to room temperature, and acetone (2 eq.) was added slowly (~1 hour). The hydrazone started to crystallize after the addition of acetone. After aging for 1 hour at room temperature, water (1.5 L/mole compound (7)) was added (~1 hour). The mixture was aged for 1 hour, filtered, and washed twice with water and dried at +40° C. under vacuum to give compound (11).

A reaction vessel was charged with THF (1.25 L/mole compound (11)), compound (11) (1 eq.), tetrabutylammonium iodide (0.03 eq.), 4-chlorobenzyl chloride (1.05 eq.), and 5 N NaOH (5 eq.) under nitrogen. The resultant biphasic mixture was heated to 50° C. and stirred for 5 h. The mixture was then cooled to room temperature and the aqueous layer was cut. The organic layer was washed with 15% NaCl aqueous solution (1 L/mole compound (11)). The organic mixture was heated up to 50° C., and methanesulfonic acid (MSA, 1.1 eq.) was added over 0.5 h. After the addition was completed, 0.1 wt % of the MSA salt seed was added to initiate the crystallization. The batch was aged at 50° C. for 2 h, and MTBE (4 L/mole compound (11)) was then added over 1 h. After an additional 2 h at 50° C., the batch was cooled down to room temperature and aged for 2 h. The mixture was filtered, and the cake was washed twice with MTBE and dried at +40° C. under vacuum to give the hydrazine/MSA salt, compound (12).

Step 3. Preparation of Compound (13)

Method A

To a slurry of compound (12) (1 eq.) in acetonitrile (3.4 L/mole compound (12)) at room temperature was added the MTBE solution of compound (3) in one portion (0.813 M in MTBE, 1.1 eq.). The resulting slurry was degassed and heated up to +50-55° C. for 24 h. Water (340 mL/mole compound (12)) was added at +50° C., and the reaction mixture was allowed to cool to room temperature. The batch was filtered, rinsed with 90/10 acetonitrile/water (850 mL/mole compound (12)) and with methanol (1.7 L/mole compound (12)). The cake was dried in the oven at +40-50° C. for 24 hours to give the product.

Method B

A round-bottom flask was charged with compound (12) (1 eq.) and compound (3) diisopropylamine (DIPA) salt (eq.) and propionic acid (3.33 L/mole compound (12)) in that order at 20-25° C. The slurry was warmed to 40° C. and aged for 3 h. Methanesulfonic acid (1.2 eq.) was added over 3-5 min. The slurry was aged at 50-60° C. for 1 h, cooled to 30° C. and water (0.33 L/mole compound (12)) added over approx 5 min. The slurry was aged for 30 min and filtered. The pale yellow cake was washed with 10% aqueous methanol (10% water, 90% methanol, 2 L/mole compound (12)) until the filtrate was colorless. The cake was washed with ethanol (1 L/mole compound (12)). The cake was dried in $N_2$ flow and then in a vacuum oven at 40C to give the product.

Preparation of Compound (13) TMG Salt:

1,1,3,3-Tetramethylguanidine (TMG, 99%, 24.5 mL, 193 mmol) was charged to a slurry of compound (13) (70 g, 161 mmol) in isopropylacetamide (IPAc, 280 mL) and MeOH (140 mL) at 23° C., whereupon the solids dissolved. Additional IPAc (125 mL) was added with seeded, resulting in the formation of a slurry. Additional IPAc (125 mL) was added and the mixture aged overnight. The slurry was distilled at constant volume by the simultaneous addition of IPAc. When the supernatant reached 5 mg/mL, distillation was discontinued and the slurry cooled in an ice batch. The crystals were filtered, washing with ice-cold IPAc. Drying yielded 85.6 g of crystalline solid which was 96.8 wt % purity.

Preparation of Compound (13) DBU Salt:

DBU (99%, 0.21 mL, 1.36 mmol) was charged to a slurry of compound (13) (0.50 g, 1.2 mmol) in MeOH (3 mL) at 60° C. The, now homogeneous, solution was cooled to 23° C. and seeded, resulting in the formation of a slurry. MTBE (6 mL) was added and the slurry aged overnight. The solids were filtered, washing with 4:1 MTBE/MeOH. Drying the solids yielded 0.57 g of compound (13) DBU salt.

Preparation of Compound (13) DBN Salt:

DBN (98%, 0.33 mL, 2.65 mmol) was charged to a slurry of compound (13) (1.00 g, 2.30 mmol) in MeOH (5 mL) at 60° C. The, now homogeneous, solution was cooled to 23° C., whereupon. MTBE (4 mL) was added slowly with periodic seeding. The resultant slurry was aged for 60 min. Additional MTBE (11 mL) was added to the slurry, and aged further. The solids were filtered, washing with 5:1 MTBE/MeOH. Drying the solids yielded 0.98 g of compound (13) DBN salt.

Preparation of Compound (13) Potassium Salt:

KOtBu (95%, 285 mg, 2.41 mmol) was charged to a slurry of compound (13) (1.00 g, 2.30 mmol) in MeOH (5 mL) at 23° C. MTBE (5 mL) was added slowly to the solution and the resultant turbid solution was filtered through a 0.45 µm syringe filter. Additional MTBE was added to the filtrate, resulting in the formation of a slurry. The slurry was aged for 60 min. The solids were filtered, washing with 5:1 MTBE/MeOH and then 100% MTBE. Drying the solids yielded 0.58 g of compound (13) potassium salt.

REFERENCE EXAMPLE 2

In Situ Catalyst Formation

Ruthenium In an inert atmosphere glove box, degassed methanol (75 mL) is charged to a round bottom flask containing [(p-cymene)RuCl$_2$]$_2$ (0.369 g, 0.60 mmol) and (S)-BINAP (0.770 g, 1.24 mmol). Degassed toluene (25 mL) is added and the orange heterogeneous solution is transferred to an ampoule with a re-sealable Kontes adapter. The ampoule is sealed, removed from the glove box, and heated for 1-2 hours at 50-60° C. with stirring. The clear, orange solution is brought into a glovebox and stored at room temperature as a stock solution (approx. molarity of [(p-cymene)(S-BINAP)RuCl$_2$]=0.012).

Rhodium In an inert atmosphere glove box, previously degassed methanol is charged to a round bottom flask containing Rh(COD)$_2$BF$_4$ and the desired chiral ligand (1.1 molar equiv L/Rh). The solution is stirred for 1 hour at room temperature. [catalyst]=0.016 M.

The following non-limiting examples are provided to further illustrate the invention.

EXAMPLE 1

[(3R)-4-(4-Chlorophenyl)methyl-7-fluoro-5-(methylsulfonyl)-1,2,3,4-tetrahydrocyclopenta[b] indol-3-yl] acetic acid, TMG and DIPA salts

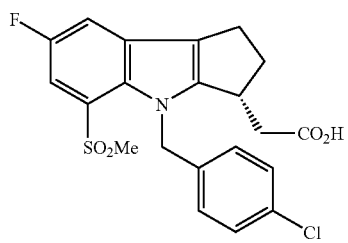

TMG Salt

Method A. A reaction pressure vessel is charged with compound (13) (3.0 g, 6.9 mmol), MeOH (23 mL), and a stirbar. The tan slurry is set stirring and TMG (0.8 mL, 6.9 mmol) is added via syringe. The resulting purple/brown slurry is degassed (vac/nitrogen×5) and the vessel is brought into a glovebox. The ruthenium catalyst, [(p-cymene)(S-BINAP)RuCl$_2$]$_2$ (8.1 mL, 0.012 M in methanol/toluene (3:1), 1.4 mol %), is charged via syringe. The vessel is sealed, removed from the glovebox, and attached to a hydrogen/nitrogen/vacuum manifold. After degassing (vac/nitrogen×5) the lines leading up to the pressure vessel, the stirred solution in the pressure vessel is degassed (nitrogen/vac×3), and pressure purged with hydrogen gas without stirring (hydrogen 40 psig/vac×3). The reaction solution is then placed under hydrogen gas (10 psig), set stirring, and warmed to 45-50° C. After aging overnight (~15 h), the resulting homogeneous solution is cooled to room temperature and the pressure vessel is vented to atmospheric pressure. ee=91%.

Method B. In a glove box, a reaction pressure vessel is charged with compound (13) TMG salt (2.5 g, 4.6 mmol), degassed MeOH (25 mL), [(p-cymene)(S-BINAP)RuCl$_2$]$_2$ (1.9 mL, 0.023 mmol, 0.5 mol %), and a stirbar. The vessel is sealed, removed from the glovebox, and attached to a hydrogen/nitrogen/vacuum manifold. After degassing (vac/nitrogen×5) the lines leading up to the pressure vessel, the pressure vessel is degassed (nitrogen/vac×5). The vessel is heated to 53° C., pressure purged with hydrogen gas (hydrogen/vac×3) and placed under hydrogen gas (10 psig). The stirred slurry is aged overnight (~15 h) and then cooled to room temperature and the pressure vessel is vented to atmospheric pressure. ee=91%.

DIPA Salt

A slurry containing compound (13) (1.0 eq.) and EtOH (1 L/mole compound (13)) was degassed via a nitrogen sparge. This slurry is charged to the autoclave via vacuum along with degassed Et$_3$N (1.0 eq) a degassed EtOH (0.5 L/mole compound (13)) rinse. Via a double bomb set-up (500 mL & 150 mL) pre-degassed 45% KOH (1.0 eq) is charged to the autoclave followed by degassed EtOH (100 mL) as a rinse. Then pre-degassed EtOH (100 mL) from a separate Schlenk flask is charged through the same line that will be used for the catalyst charge. This EtOH charge is necessary to completely clear the charge line of any KOH that would harm the catalyst. The mixture is degassed via a nitrogen-vacuum purge and via a double bomb set-up (2 L & 150 mL) 0.012M S-BINAPRuCl$_2$-p-cymene complex in 3:1 EtOH-toluene (0.5 mol %) is charged to the autoclave followed by a EtOH (100 mL) rinse. The mixture is degassed via 3 nitrogen-pressure purges and then with 3 hydrogen-pressure purges at 28-27C. The mixture is then hydrogenated at 20 psig at 50C until reaction is judged complete (HPLC: <0.1A % compound (13) remaining).

A round bottom flask was charged with the crude hydrogenation stream (164 mg/mL, 1 eq. of chiral free acid). The solution was diluted with ethanol (2.9 L/mole free acid) and DIPA (2 eq.) was added. The solution was warmed to 55° C. Propionic acid (2 eq.) was added over approx 1 h at 55° C. The slurry was aged at 55° C. for 1 h, cooled to 20° C. over 1 h and aged for 1 h. The slurry was filtered and the cake washed with cold (5° C.) ethanol (1.74 L/mole free acid) and ethyl acetate (1.45 L/mole free acid). The cake was dried in N$_2$ flow for 1 h and in vacuo at 35-45° C.

EXAMPLE 2

Hydrogenation Procedure using Rhodium Catalyst

In an inert atmosphere glove box, rhodium catalyst solution (0.016 M in methanol) is transferred to a pressure vessel containing compound (13) and base (e.g., TMG) in methanol. The vessel is sealed, removed from the glovebox, and attached to a hydrogen/nitrogen/vacuum manifold. After degassing (vac/nitrogen×5) the lines leading up to the pressure vessel, the pressure vessel is degassed (nitrogen/vac×5). The vessel is pressure purged with hydrogen gas (hydrogen/vac×3) and placed under hydrogen gas (90 psig). The stirred slurry is aged overnight (~15 h) and the pressure vessel is vented to atmospheric pressure and assayed.

EXAMPLE 3

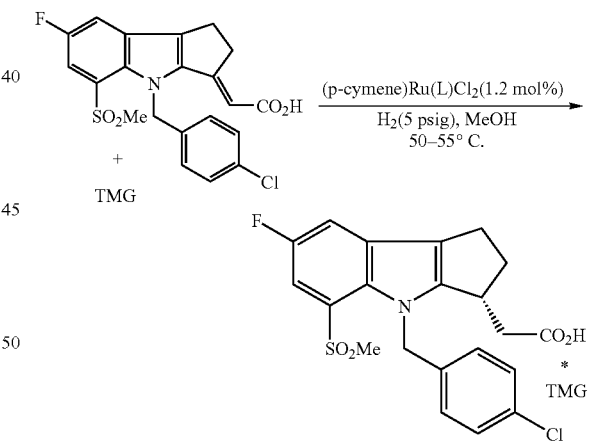

Catalysts prepared using procedure in Reference Example 2; hydrogenation performed using procedure in Example 1, method A.

| L(cymene)RuCl$_2$ | A % conv | % ee |
|---|---|---|
| BINAP | 100 | 90 |
| Solvias BINAP | 92 | −88 |
| xyl-Solvias BINAP | 100 | −89 |
| Synphos | 96 | 89 |

-continued

| L(cymene)RuCl$_2$ | A % conv | % ee |
|---|---|---|
| TMBTP | 100 | −70 |
| (R)-HexaPHEMP | 100 | −88 |
| (S)-C6-TunaPhos | 100 | 85 |

Reaction conditions: 1.2 mol % catalyst, 50° C., 15 hours, 5 psig, 100 mg compound (13)/1 mL MeOH. It is understood that when the % ee is negative, the opposite enantiomer of the catalyst used would provide the desired product.

EXAMPLE 4

Coversion of Compound of Example 1 TMG Salt to the Free Acid

The crude hydrogenation solution (105.5 g) containing 10 g assay of the product of Example 1 (95.3/4.7 ratio of enantiomer, therefore 9.53 g assay of optically pure product) was concentrated and switched to ethyl acetate (AcOEt) several times to ensure that no more residual MeOH/toluene/water remained. The volume was adjusted to 12 mL AcOEt/g TMG salt (120 mL). Water (1.25 V % relative to AcOEt: 1.5 mL) was added. The slurry was heated up to +55° C. for approximately 10 h. The slurry was allowed to cool to r.t and aged for 10 hours and filtered. The cake was rinsed with recycled mother liquor and was finally washed with AcOEt (35 mL). It was dried in the oven at +40° C. to give around 9.0 g of TMG salt with ee98.5% (8.9 g assay of optically pure TMG salt; ca. 93% yield). The dry cake (9 g; 7.1 g as free acid) was slurried in AcOEt (90 mL) and was washed with 0.5N aqueous HCl (90 mL) to become two homogeneous layers. Layers are separated and the organic was washed with water (2×75 mL). The resulting AcOEt solution was treated with Ecosorb C-941 (10 wt % loading relative to free acid, 710 mg). The slurry was aged at r.t for 1 hour and filtered through solka floc (with AcOEt rinse). The resulting colorless solution was concentrated and the volume of AcOEt was adjusted to 28.4 mL and water was added (142 μL to make KF5000). The batch was heated up to +55-60° C. to dissolve. n-Heptane (ca. 8 mL) was added slowly to crystallize. The batch was aged at +55° C. for ca. 1 hour and remaining n-heptane (105.6 mL) was added over 1-2 h at +55° C., aged a few hours and allowed to cool to r.t. Filtered, and rinsed with 80/20 n-heptane/AcOEt (~50 mL), and dried in the oven at +40° C. for 24 hours to give around 6.6 g of the product as the free acid with e.e~99.7%.

Coversion of Compound of Example 1 DIPA Salt to the Free Acid

A slurry of compound of Example 1 DIPA salt dry cake (9 g) in AcOEt (90 mL) was washed with 0.5N aqueous HCl (90 mL) to give two homogeneous layers. Layers are separated and the organic is washed with water (2×75 mL). The resulting AcOEt solution was treated with Ecosorb C-941 (10 wt % loading relative to free acid, 710 mg). The slurry is aged at r.t for 1 hour and filtered through solka floc (+AcOEt rinse). The resulting colorless solution was concentrated and the volume of AcOEt adjusted to 28.4 mL and water is added (142 μL to make KF~5000). The batch is heated up to +55-60° C. to dissolve. n-Heptane (ca. 8 mL) is added slowly to crystallize. The batch is aged at +55° C. for ca. 1 hour and remaining n-heptane (105.6 mL) is added over 1-2 h at +55° C., aged a few hours and allowed to cool to r.t. The slurry was filtered and washed with 80/20 n-heptane/AcOEt (~50 mL). Solid dried in the oven at +40° C. for 24 hours to give 6.9 g of the desired product.

What is claimed is:

1. An asymmetric hydrogenation process for the preparation of a compound of formula I or a salt thereof in at least 50% enantiomeric excess (ee)

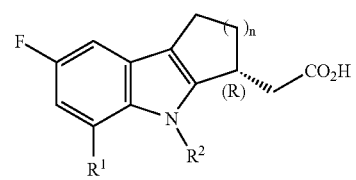

wherein n is 1 or 2, $R^1$ is Br or $SO_2CH_3$, and $R^2$ is H, benzyl, 4-nitrobenzyl, 4-aminobenzyl, 4-trifluoromethylbenzyl or 4-chlorobenzyl, which comprises: treating a compound of formula II or a salt thereof

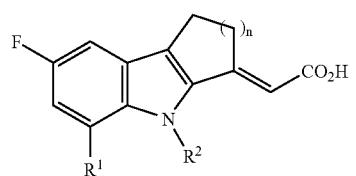

with a metal-chiral ligand and a hydrogen donor wherein when the hydrogen donor is $H_2$, the process is carried out at a pressure of from about 0 to about 500 pounds per square inch gauge (psig), and wherein said metal-chiral ligand is (a) a ruthenium-axially chiral phosphine ligand complex, or (2) a rhodium chiral ferrocenyl phosphine ligand complex, or (3) a rhodium-TMBTP complex.

2. The process of claim 1 wherein said metal-chiral ligand is ruthenium-axially chiral phosphine ligand complex and said chiral ligand is selected from BINAP (formula (a) Ar=phenyl), tol-BINAP (formula (a) Ar=p-tolyl), xyl-BINAP (formula (a) Ar=3,5-xylyl), H8-BINAP (formula (b) Ar=phenyl), SYNPHOS™ (formula (c) Ar=phenyl), SEGPHOS (formula (d) Ar=phenyl), Solvias BINAP (formula (e) Ar=phenyl), SOLVIAS xyl-BINAP (formula (e) Ar3,5-xylyl), MeO-BIPHEP (formula (f) Ar=phenyl, Z=methyl, $R^a=R^b=R^c=H$), hexaPHEMP (formula (f) Ar=phenyl, $Z=R^a=R^b$=methyl, $R^c=H$), tunaphos (formula (g) Ar=phenyl and n is 1-6), TMBTP (formula (h) Ar=phenyl), P-Phos (formula (i) Ar=phenyl), tol-P-Phos (formula (i) Ar=tolyl), xyl-P-Phos (formula (i) Ar=3,5-xylyl),

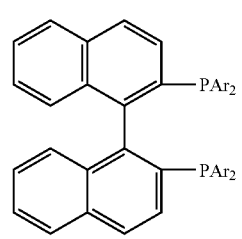

-continued (b) 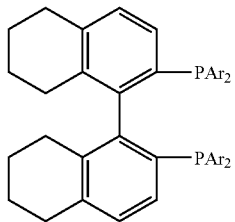

(c) 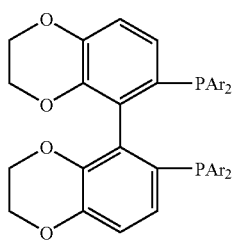

(d) 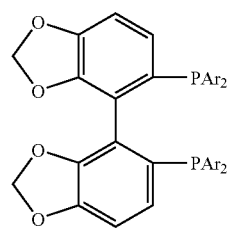

(e) 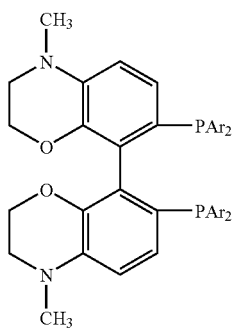

(f) 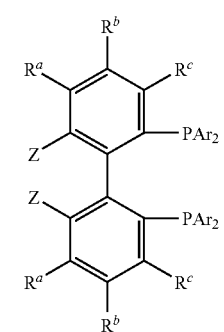

-continued (g) 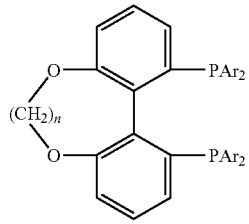

(h) 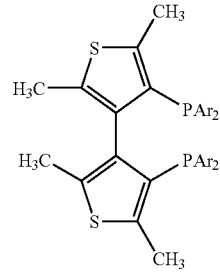

(i) 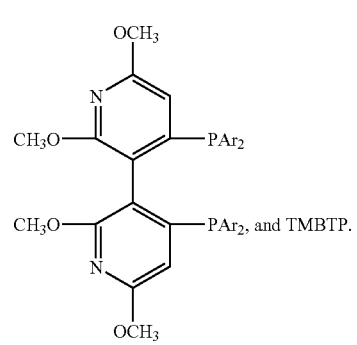

, and TMBTP.

3. The process of claim 1 wherein said metal-chiral ligand is (p-cymene)Ru(S)-BINAP-Cl$_2$.

4. The process of claim 1 wherein said metal-chiral ligand is (chiral ligand)RuX$_2$, wherein each occurrence of X is independently selected from Cl, Br, I, triflate, acetate, methanesulfonate, benzenesulfonate, BF$_4$, and B(Ar)$_4$, and Ar is phenyl, m- or p-toyl, xylyl and methoxyphenyl.

5. The process of claim 1 wherein said metal-chiral ligand is a rhodium-ferrocenyiphosphine ligand complex and said ferrocenyiphosphine ligand is selected from f-BINAPHANE of formula (m)

(m) 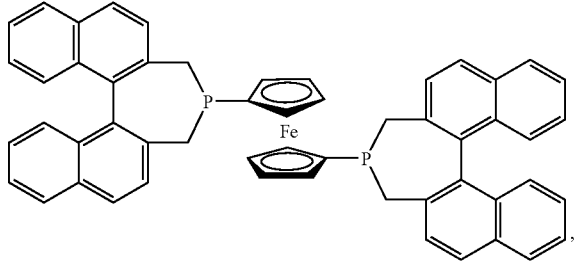

,

Walphos (formula (j) wherein $R_d$ and $R_e$ are each methyl or trifluoromethyl)

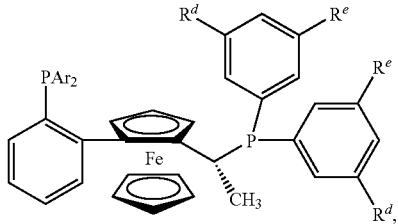

the josiphos of formula (k)

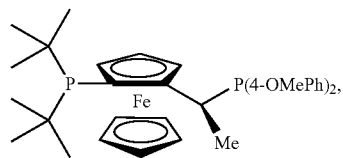

the taniaphos of formula (l)

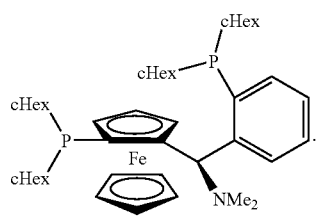

6. The process of claim 1 wherein said metal-chiral ligand is a rhodium-TMBTP complex.

7. The process of claim 1 wherein said hydrogenation is carried out in the presence of a base and optionally in the presence of a Group I or Group II salt.

8. An asymmetric hydrogenation process for the preparation of a compound of formula Ia or a salt thereof in at least 50% enantiomeric excess (ee)

Ia

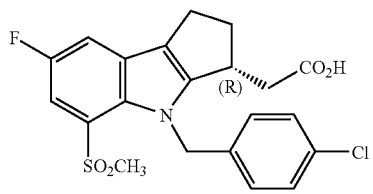

which comprises: treating a compound of formula IIa or a salt thereof

IIa

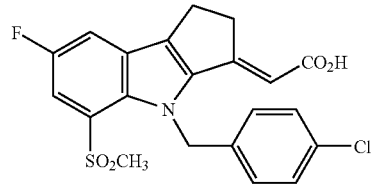

with a metal-chiral ligand and a hydrogen donor wherein when the hydrogen donor is $H_2$, the process is carried out at a pressure of from about 0 to about 500 pounds per square inch gauge (psig), and wherein said metal-chiral ligand is (a) a ruthenium-axially chiral phosphine ligand complex, or (2) a rhodium chiral ferrocenyl phosphine ligand complex, or (3) a rhodium-TMBTP complex.

9. The process of claim 8 wherein said hydrogenation is carried out with hydrogen in the presence of a base, and wherein said metal-chiral ligand is selected from (1) ruthenium complex with BINAP (formula (a) Ar=phenyl), tol-BINAP (formula (a) Ar=-tolyl), xyl-BINAP (formula (a) Ar=3,5-xylyl), $H_8$-BINAP (formula (b) Ar=phenyl), SYN-PHOS™ (formula (c) Ar=phenyl), SEGPHOS (formula (d) Ar=phenyl), Solvias BINAP (formula (e) Ar=phenyl), SOLVIAS xyl-BINAP (formula (e) Ar3,5-xylyl), MeO-BI-PHEP (formula (f) Ar=phenyl, Z=methyl, $R^a=R^b=R^cH$), hexaPHEMP (formula (f) Ar=phenyl, Z=$R^a$=$R^b$=methyl, $R^c$=H), tunaphos (formula (g) Ar=phenyl and n is 1-6), TMBTP (formula (h) Ar=phenyl), P-Phos (formula (i) Ar=phenyl), tol-P-Phos (formula (i) Ar=tolyl), xyl-P-Phos (formula (i) Ar3,5-xylyl)

(a)

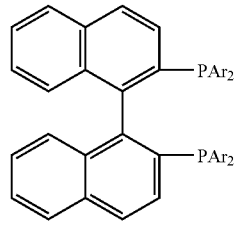

(b)

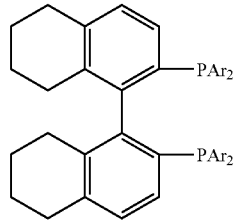

(c)

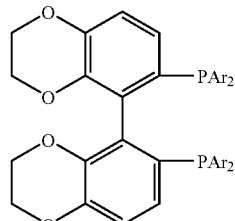

(d)

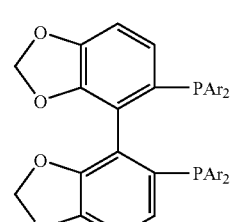

-continued
(e)
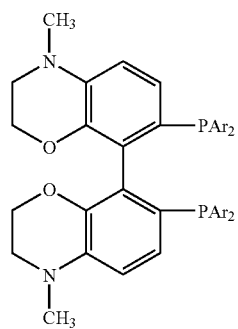
(f)
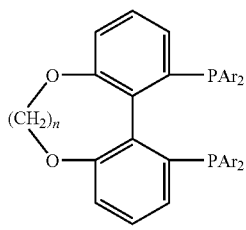
(g)
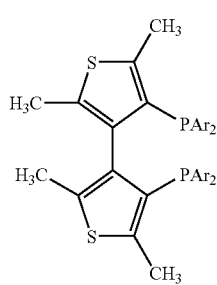
(h)
-continued
(i)
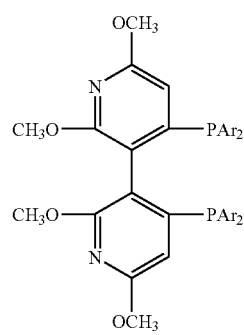
(2) rhodium complex with from f-BINAPHANE of formula (m)
(m)
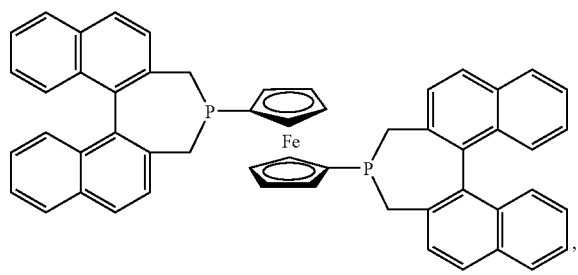
Walphos (formula (i) wherein $R_d$ and $R_e$ are each methyl or trifluoromethyl)
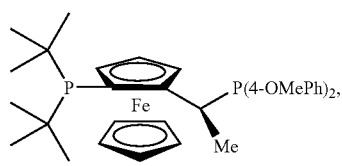
the josiphos of formula (k)
the taniaphos of formula (l)

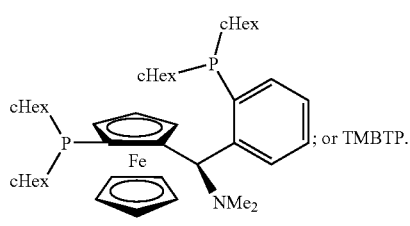
; or TMBTP.
10. The process of claim 8 wherein said hydrogenation is carried out at a pressure of from about 0 to about 20 psig.
11. A compound of the formula II or a salt thereof:
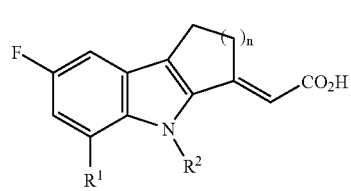
wherein n, $R^1$ and $R^2$ are as defined in claim 1.
12. The compound of claim 11 or a salt thereof, wherein n is 1, $R^1$ is —$SO_2CH_3$, and $R^2$ is 4-chlorobenzyl.
* * * * *